(12) United States Patent
Kano et al.

(10) Patent No.: US 8,361,923 B2
(45) Date of Patent: Jan. 29, 2013

(54) PROCESS FOR PRODUCING COMPLEX OXIDE CATALYST

(75) Inventors: Hirotsugu Kano, Niihama (JP); Eiichi Shiraishi, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 146 days.

(21) Appl. No.: 12/893,131

(22) Filed: Sep. 29, 2010

(65) Prior Publication Data

US 2011/0077148 A1 Mar. 31, 2011

(30) Foreign Application Priority Data

Sep. 30, 2009 (JP) ................................. 2009-226690

(51) Int. Cl.
*B01J 23/00* (2006.01)
*B01J 21/00* (2006.01)
*B01J 20/00* (2006.01)
*B01J 29/00* (2006.01)
*B01J 37/00* (2006.01)
*B01J 35/00* (2006.01)

(52) U.S. Cl. ............... 502/311; 502/20; 502/22; 502/26; 502/33; 502/107; 502/110; 502/111; 502/113; 502/305; 502/306; 502/307; 502/308; 502/309; 502/310; 502/312; 502/313; 502/314; 502/315; 502/316; 502/317; 502/321

(58) Field of Classification Search .................... 502/20, 502/22, 26, 33, 107, 110, 111, 113, 305–317, 502/321
See application file for complete search history.

(56) References Cited

U.S. PATENT DOCUMENTS

| | | | | |
|---|---|---|---|---|
| 4,052,332 A * | 10/1977 | D'Amore et al. | ................ | 502/27 |
| 4,123,453 A * | 10/1978 | Grasselli et al. | ................ | 502/211 |
| 4,156,660 A * | 5/1979 | Grasselli et al. | ................ | 502/212 |
| 4,250,339 A | 2/1981 | Sakamoto et al. | | |
| 4,330,429 A * | 5/1982 | Sasaki et al. | ................ | 502/26 |
| 4,537,874 A | 8/1985 | Sato et al. | | |
| 5,087,596 A * | 2/1992 | Clark et al. | ................ | 502/49 |
| 5,134,105 A * | 7/1992 | Paparizos et al. | ................ | 502/205 |
| 5,151,391 A * | 9/1992 | Fu et al. | ................ | 502/27 |
| 6,383,973 B1 | 5/2002 | Kimura et al. | ................ | 502/300 |
| 6,559,085 B1 * | 5/2003 | Sasaki et al. | ................ | 502/22 |
| 6,583,316 B1 * | 6/2003 | Onodera et al. | ................ | 562/537 |
| 6,982,343 B2 * | 1/2006 | Chaturvedi et al. | ................ | 558/323 |
| 7,262,148 B2 * | 8/2007 | Teshigahara et al. | ......... | 502/224 |
| 7,365,041 B2 * | 4/2008 | Miyaki et al. | ................ | 502/311 |
| 7,387,982 B2 * | 6/2008 | Kondo et al. | ................ | 502/311 |
| 7,414,008 B2 * | 8/2008 | Yunoki | ................ | 502/311 |
| 7,419,928 B2 * | 9/2008 | Malek et al. | ................ | 502/20 |
| 7,456,129 B2 * | 11/2008 | Fukumoto et al. | ............ | 502/248 |
| 7,544,633 B2 * | 6/2009 | Kang et al. | ................ | 502/311 |
| 7,632,777 B2 * | 12/2009 | Teshigahara et al. | ......... | 502/311 |
| 7,956,000 B2 * | 6/2011 | Jansen et al. | ................ | 502/27 |
| 2001/0003727 A1 * | 6/2001 | Tanimoto et al. | ............ | 502/304 |
| 2002/0103077 A1 | 8/2002 | Kimura et al. | | |
| 2002/0115879 A1 | 8/2002 | Hinago et al. | | |
| 2003/0065216 A1 * | 4/2003 | Tanimoto et al. | ............ | 562/532 |
| 2003/0153786 A1 * | 8/2003 | Tanimoto et al. | ............ | 562/535 |
| 2004/0192973 A1 | 9/2004 | Liang et al. | | |
| 2004/0204504 A1 * | 10/2004 | Malek et al. | ................ | 518/717 |
| 2004/0248734 A1 * | 12/2004 | Miyaki et al. | ................ | 502/311 |
| 2004/0267048 A1 * | 12/2004 | Kondo et al. | ................ | 562/546 |
| 2005/0187406 A1 | 8/2005 | Kang et al. | | |
| 2006/0205978 A1 * | 9/2006 | Yunoki et al. | ................ | 562/534 |
| 2006/0234861 A1 * | 10/2006 | Fukumoto et al. | ............ | 502/232 |
| 2007/0167657 A1 | 7/2007 | Kauffman et al. | | |
| 2007/0249491 A1 | 10/2007 | Liang et al. | | |
| 2009/0234158 A1 * | 9/2009 | Sudo et al. | ................ | 562/524 |

FOREIGN PATENT DOCUMENTS

| | | |
|---|---|---|
| EP | 0714697 A1 | 6/1996 |
| JP | 07-010802 A | 1/1995 |
| JP | 07-051570 A | 2/1995 |
| JP | 2002-239382 A | 8/2002 |
| JP | 2005-169311 A | 6/2005 |
| JP | 2005-187460 A | 7/2005 |
| JP | 2006-061888 A | 3/2006 |
| JP | 2006-314986 A | 11/2006 |
| JP | 2008-231044 A | 10/2008 |

OTHER PUBLICATIONS

UK Search Report issued Jan. 13, 2011 in UK Appln. No. GB1016257.6.
Search Report and Written Opinion issued May 16, 2012 in SG Application No. 201007146-2.

* cited by examiner

*Primary Examiner* — Cam N. Nguyen
(74) *Attorney, Agent, or Firm* — Panitch Schwarze Belisario & Nadel LLP

(57) ABSTRACT

A process is provided for producing a complex oxide catalyst which exhibits superior catalytic activity in a vapor phase catalytic oxidation reaction, particularly in production of unsaturated aldehyde and unsaturated carboxylic acid. The process is characterized by the steps of preparing an aqueous slurry by mixing a complex oxide containing molybdenum and cobalt with an acid and water; drying the aqueous slurry; and calcining the resulting dried solid. Preferably, the complex oxide is obtained as follows: a molybdenum- and cobalt-containing complex oxide catalyst which has been used in a vapor phase catalytic oxidation reaction is mixed with an aqueous extracting solution obtained by dissolving at least one of ammonia and an organic base in water, to thereby extract molybdenum and cobalt into the aqueous phase; and the aqueous phase is dried and is then calcined under an atmosphere of an oxidizing gas.

11 Claims, No Drawings

PROCESS FOR PRODUCING COMPLEX OXIDE CATALYST

BACKGROUND OF THE INVENTION

1. Field of the Invention

The present application claims the Paris Convention priority based on Japanese Patent Application No. 2009-226690 filed on Sep. 30, 2009, the entire content of which is incorporated herein by reference.

The present invention relates to a process for producing a complex oxide catalyst, using a complex oxide containing molybdenum and cobalt as a raw material.

2. Description of the Related Art

Complex oxide catalysts containing molybdenum and cobalt hitherto have been widely used. Examples of such complex oxide catalysts include a complex oxide catalyst for use in production of acrolein and acrylic acid by vapor phase catalytic oxidization of propylene with a molecular oxygen (Patent Publications 1 and 2); a complex oxide catalyst for use in production of acrylic acid by vapor phase catalytic oxidization of propane with a molecular oxygen (Patent Publication 3); a complex oxide catalyst for use in production of acrylonitrile by vapor phase catalytic ammoxidation of propylene or propane with a molecular oxygen and ammonia (Patent Publications 3 to 5); a complex oxide catalyst for use in production of methacrolein and methacrylic acid by vapor phase catalytic oxidization of isobutylene or tertiary butyl alcohol with a molecular oxygen (Patent Publication 1); a complex oxide catalyst for use in production of methacrylonitrile by vapor phase catalytic ammoxidation of isobutylene or tertiary butyl alcohol with a molecular oxygen and ammonia (Patent Publications 4 and 5); and a complex oxide catalyst for use in production of acrylic acid by vapor phase catalytic oxidization of acrolein with a molecular oxygen (Patent Publication 6).

In general, any of these complex oxide catalysts is obtained by mixing raw materials for catalyst with water to form an aqueous solution or aqueous slurry, drying the resulting aqueous solution or aqueous slurry, and calcining the resultant dried solid. As the raw materials for such a catalyst, compounds each containing one of the respective elements which constitute the catalyst are used in required amounts. That is, there are used, as the raw materials, a molybdenum-containing compound, a cobalt-containing compound, and optionally, a compound which contains a catalyst-constituting element other than molybdenum and cobalt (cf. Patent Publications 1 to 6).

Patent Publication 1: JP-A-2008-231044
Patent Publication 2: JP-A-2005-187460
Patent Publication 3: JP-A-2002-239382
Patent Publication 4: JP-A-2006-061888
Patent Publication 5: JP-A-7-51570
Patent Publication 6: JP-A-7-10802

However, the complex oxide catalysts obtained by the conventional processes are not always sufficient in their catalytic activities in the vapor phase catalytic oxidation reactions, especially in production of unsaturated aldehyde and unsaturated carboxylic acid.

An object of the present invention is therefore to provide a process for producing a complex oxide catalyst which exhibits a superior catalytic activity in vapor phase catalytic oxidation reaction, especially in production of unsaturated aldehyde and unsaturated carboxylic acid.

SUMMARY OF THE INVENTION

As a result of the present inventors' intensive studies, it is found that a complex oxide catalyst with sufficient catalytic activity can be produced by the use of a complex oxide containing molybdenum and cobalt as a raw material for catalyst, that is, by mixing this complex oxide with an acid and water to prepare aqueous slurry, drying this aqueous slurry, and calcining the resulting dried solid. The present invention is accomplished based on this finding.

That is, the present invention provides the following.

(1) A process for producing a complex oxide catalyst containing molybdenum and cobalt, characterized by the steps of mixing a complex oxide containing molybdenum and cobalt, with an acid and water, to prepare aqueous slurry; drying the aqueous slurry; and calcining the resulting dried solid.

(2) The process defined in the item (1), wherein the complex oxide is obtained by mixing a molybdenum- and cobalt-containing complex oxide catalyst which has been used in a vapor phase catalytic oxidation reaction, with an aqueous extracting solution obtained by dissolving at least one of ammonia and an organic base in water, to thereby extract molybdenum and cobalt in an aqueous phase; drying this aqueous phase; and calcining the resulting dried solid under an atmosphere of an oxidizing gas.

(3) The process defined in the item (1) or (2), wherein a ratio of molybdenum to cobalt in the complex oxide is from 1:12 to 12:1 in molar ratio.

(4) The process defined in any one of the items (1) to (3), wherein the complex oxide contains at least one element selected from the group consisting of potassium, rubidium, cesium and thallium.

(5) The process defined in any one of the items (1) to (4), wherein the amount of the acid to be used is from 1 to 20 moles per one mole of cobalt in the complex oxide.

(6) The process defined in any one of the items (1) to (5), wherein the acid is an inorganic acid.

(7) The process defined in any one of the items (1) to (5), wherein the acid is nitric acid.

(8) The process defined in any one of the items (1) to (7), wherein the complex oxide catalyst is for use in production of unsaturated aldehyde and unsaturated carboxylic acid.

(9) The process defined in any one of the items (1) to (8), wherein the complex oxide catalyst is represented by the following formula (I):

$$Mo_aBi_bFe_cCo_dA_eB_fC_gO_x \quad (I)$$

wherein, in the formula (I), Mo, Bi, Fe and Co represent molybdenum, bismuth, iron and cobalt, respectively; A represents an element selected from the group consisting of nickel, manganese, zinc, calcium, magnesium, tin and lead; B represents an element selected from the group consisting of phosphorus, boron, arsenic, tellurium, tungsten, antimony, silicon, aluminum, titanium, zirconium and cerium; C represents an element selected from the group consisting of potassium, rubidium, cesium and thallium; O represents oxygen; b, c, d, e, f and g are values satisfying the following equations, provided that a is 12 (a=12): $0<b\leq10$, $0<c\leq10$, $1\leq d\leq10$, $0\leq e\leq10$, $0\leq f\leq10$ and $0<g\leq2$; and x is a value determined by the oxidation states of the respective elements.

(10) The process defined in any one of the items (1) to (9), wherein the aqueous slurry is dried and calcined and is then subjected to a heat treatment in the presence of a reducing substance.

(11) The process defined in the item (10), wherein the heat treatment is carried out at a temperature of from 200 to 600° C.

(12) The process defined in the item (10) or (11), wherein a rate of decrease in mass, attributed to the heat treatment, is from 0.05 to 6% by mass.

(13) The process defined in any one of the items (10) to (12), wherein the reducing substance is hydrogen.

According to the present invention, there can be produced a complex oxide catalyst which exhibits a superior catalytic activity in a vapor phase catalytic oxidation reaction, especially in production of unsaturated aldehyde and unsaturated carboxylic acid. Again, according to the present invention, a complex oxide catalyst which exhibits a superior catalytic activity can be produced by using, as raw materials, molybdenum and cobalt which are recovered from, for example, a molybdenum- and cobalt-containing catalyst which has been used for a vapor phase catalytic oxidation reaction.

DETAILED DESCRIPTION OF THE INVENTION

Hereinafter, the present invention will be described in detail. A complex oxide catalyst according to the present invention can be produced by using a molybdenum- and cobalt-containing complex oxide as a raw material. The complex oxide as the raw material may be, for example, a complex oxide which contains only molybdenum and cobalt as metal elements to be contained, or may be a complex oxide which contains one or two or more constitutive metal elements other than molybdenum and cobalt, together with molybdenum and cobalt. Examples of other metal elements constituting the complex oxide include bismuth, iron, nickel, manganese, zinc, calcium, magnesium, tin, lead, phosphorus, boron, arsenic, tellurium, tungsten, antimony, silicon, aluminum, titanium, zirconium, cerium, potassium, rubidium, cesium, thallium, vanadium, copper, silver, lanthanum, etc., among which potassium, rubidium, cesium and thallium are preferable.

A ratio of molybdenum to cobalt in the complex oxide is usually from 1:12 to 12:1, preferably from 1:5 to 5:1, more preferably from 1:3 to 3:1 (in molar ratio).

The contents of the metal elements in the complex oxide can be determined, for example, by X-Ray fluorescence analysis.

The molybdenum- and cobalt-containing complex oxide of the present invention may be prepared from a molybdenum compound and a cobalt compound; or the same complex oxide may be prepared from catalyst-constituting elements recovered from a spent catalyst or the like; or the same complex oxide may be prepared from catalyst-constituting elements recovered from a complex oxide which has no desired performance although produced as a catalyst or the like (e.g., a complex oxide which has been powdered during the production steps, or a complex oxide which has deteriorated due to a thermal load or the like). However, a Keggin type heteropolyacid is excluded from these complex oxides. Above all, the use of a complex oxide obtained from catalyst-constituting elements recovered from the complex oxide already used as a catalyst or the like is preferable. The kind of a catalyst for use in recovery of the catalyst-constituting elements is not limited: i.e., examples of such a catalyst are catalysts for use in vapor phase catalytic oxidation reactions, such as a catalyst for use in production of unsaturated aldehyde and unsaturated carboxylic acid, and a catalyst for use in production of unsaturated carboxylic acid; catalysts for use in vapor phase catalytic ammoxidations, such as a catalyst for use in production of unsaturated nitrile; a catalyst for use in desulfurization of heavy oil; a catalyst for use in denitrification of heavy oil; and catalysts for use in hydrogen treatments of heavy oil, such as a catalyst for use in reforming (hydrogenolysis) and a catalyst for use in hydrogenation.

As a method for recovering the catalyst-constituting elements from the complex oxide used as the catalyst or the complex oxide which has no desired performance although produced as a catalyst, such a complex oxide is mixed with an aqueous extracting solution obtained by dissolving at least one basic component of ammonia and an organic base in water (hereinafter optionally referred to as an extraction treatment). By mixing the complex oxide with the aqueous extracting solution, molybdenum and cobalt are extracted into the aqueous phase of the aqueous extracting solution efficiently.

When the basic component is ammonia, a compound which is decomposed to form ammonia (hereinafter optionally referred to as "an ammonia-forming substance") may be dissolved in water, instead of the use of ammonia. As the ammonia-forming substance, there are exemplified ammonium carbonate, ammonium hydrogencarbonate, urea, etc. Each of these ammonia-forming substances may be used alone, or two or more thereof may be used in combination.

When the basic component is an organic base, there are exemplified, as the organic base, amines such as saturated aliphatic amines (e.g., methylamine, dimethylamine, trimethylamine, ethylamine, diethylamine and triethylamine), unsaturated aliphatic amines (e.g., allyamine, diallylamine and triallylamine) and aromatic amines (e.g., aniline); quaternary ammonium compounds such as hydroxides and halides of quaternary ammonium (e.g., tetramethylammonium, tetraethylammonium, n-propyltrimethylammonium, tetra-n-propylammonium, tetra-n-butylammonium, 4,4'-trimethylenebis(dimethylpiperidium), benzyltrimethylammonium, dibenzyldimethylammonium, 1,1'-butylenebis(4-aza-1-azoniabicyclo[2,2,2]octane), trimethyladamantylammonium, etc.); pyridine; and the like. Among those, at least, one of the amines and the quaternary ammonia compounds is preferably used. Each of these organic bases may be used alone, or two or more thereof may be used in combination.

The number of moles of the basic component to be dissolved in the aqueous extracting solution should be larger than the number of total moles of molybdenum and cobalt in the complex oxide which is mixed with the same aqueous extracting solution. Specifically, a ratio of the number of moles of the basic component to the number of total moles of molybdenum and cobalt is one or more, preferably 2 or more. As the aqueous extracting solution, an aqueous ammonia solution is preferably used in view of cost.

The pH of the aqueous extracting solution is preferably 8 or more. When this pH is smaller than 8, the recovery of molybdenum and cobalt tends to be insufficient.

The temperature for the extraction treatment is preferably from 0 to 100° C., more preferably from 10 to 80° C. The time for the extraction treatment is usually from one minute to 100 hours, preferably from 1 to 24 hours.

In the extraction treatment, the order or method for mixing the complex oxide catalyst and the aqueous extracting solution is not limited: for example, one of the aqueous extracting solution and the complex oxide may be added to the other thereof; or one of the aqueous extracting solution and a previously prepared aqueous dispersion of the complex oxide in water may be added to the other thereof; or at least one of ammonia (or an ammonia-forming substance) and the organic base may be dissolved in a previously prepared aqueous dispersion of the complex oxide in water. In this regard, preferably, the complex oxide is ground before the mixing.

As a result of the extraction treatment, there are obtained an aqueous phase containing the extracted molybdenum and cobalt (hereinafter optionally referred to as "a molybdenum- and cobalt-containing aqueous solution") and a solid residue derived from the complex oxide. The molybdenum- and cobalt-containing aqueous solution and the residue, thus recovered, are usually obtained as slurry. Accordingly, this slurry is decanted or filtered, for example, by natural filtration, filtration under reduce pressure, pressure filtration or centrifugal filtration, to thereby take out only the molybdenum- and cobalt-containing aqueous solution. The molybdenum- and cobalt-containing aqueous solution is dried and is then calcined under an atmosphere of an oxidizing gas, to obtain a complex oxide which contains molybdenum and cobalt.

Conditions for drying and calcining the above-described molybdenum- and cobalt-containing aqueous solution are not limited. Such conditions may be appropriately selected in accordance with a process for producing a known complex oxide or a known complex oxide catalyst.

When ammonia is used as the basic component, the ammonia may be separately recovered and recycled.

When the complex oxide catalyst for use in the above-described extraction treatment contains cesium together with molybdenum and cobalt, the cesium also can be efficiently extracted into the aqueous phase and thus can be recovered well.

In this way, the molybdenum- and cobalt-containing complex oxide can be prepared. In the present invention, this complex oxide is used as a raw material for a catalyst, and is mixed with an acid and water to form aqueous slurry; and this aqueous slurry is dried and is then calcined.

As the acid, there are exemplified inorganic acids such as nitric acid, sulfuric acid, hydrochloric acid, phosphoric acid and boric acid; and organic acids such as formic acid, acetic acid, propionic acid, butylic acid, valeric acid, hexanoic acid, benzoic acid, oxalic acid, maloic acid, succinic acid, adipic acid and phthalic acid, among which nitric acid is preferable. Each of these acids may be used alone, or two or more thereof may be used in combination.

The acid may be used as it is, or may be used in the form of an aqueous solution. The amount of the acid to be used may be so selected as to be larger than the number of moles of cobalt in the above-described complex oxide. Specifically, the amount of the acid is usually from 1 to 20 moles, preferably from 2 to 10 moles, per one mole of cobalt.

The temperature for mixing the complex oxide with the acid and water to form aqueous slurry is preferably from 0 to 100° C., more preferably from 10 to 80° C. The mixing time may be appropriately selected in accordance with the mixing temperature, etc., and it is usually from one minute to 100 hours, preferably from 1 to 24 hours.

When the aqueous slurry is prepared by mixing the complex oxide with the acid and water, the order and method for mixing them are not limited. The complex oxide, the acid and water may be mixed in an optional order: for example, one of the acid and a previously prepared aqueous dispersion of the complex oxide in water may be added to the other thereof; or one of the complex oxide and a previously prepared aqueous solution of the acid in water may be added to the other thereof; or one of a previously prepared aqueous dispersion of the complex oxide in water and a previously prepared aqueous solution of the acid in water may be added to the other thereof. Preferably, the complex oxide is ground before the mixing.

The aqueous slurry obtained by mixing the complex oxide with the acid and water may be singly dried and calcined; or a material compound for introducing a metal element other than molybdenum and cobalt may be added to the aqueous slurry at a suitable timing, that is, before the mixing, before the drying or before the calcining. By addition of a predetermined amount of such a material compound, it becomes possible to desirably adjust a composition ratio of the resultant complex oxide catalyst.

As the material compound for introducing a metal element other than molybdenum and cobalt, there may be used any of the compounds, for example, the oxides, nitrates, sulfates, carbonates, hydroxides, oxo-acids or ammonium salts thereof, and halides, of metal elements such as bismuth, iron, nickel, manganese, zinc, calcium, magnesium, tin, lead, phosphorus, boron, arsenic, tellurium, tungsten, antimony, silicon, aluminum, titanium, zirconium, cerium, potassium, rubidium, cesium, thallium, vanadium, copper, silver and lanthanum.

It is also possible to adjust the composition ratio of the resultant complex oxide by adding a material compound for introducing molybdenum or cobalt, when a metal element other than molybdenum and cobalt is introduced. As a material compound for introducing molybdenum, there are exemplified molybdenum compounds such as molybdenum trioxide, molybdic acid and ammonium paramolybdate. As a material compound for introducing cobalt, there are exemplified cobalt compounds such as cobalt nitrate and cobalt sulfate.

In the process for producing the complex oxide catalyst of the present invention, conditions for the drying and calcining of the above-described aqueous slurry are not limited. In accordance with the kind (or end use) of a desired catalyst, publicly known conditions are appropriately employed for the process for producing the catalyst of the present invention. For example, when an intended complex oxide catalyst is for use in production of unsaturated aldehyde and unsaturated carboxylic acid, any of the methods and conditions disclosed in JP-A-2007-117866, JP-A-2007-326787, JP-A-2008-6359, JP-A-2008-231044, etc. may be appropriately employed. When an intended complex oxide catalyst is for use in production of unsaturated nitrile, any of the methods and conditions disclosed in JP-B-48-43096, JP-B-59-16817, etc. may be appropriately employed. When an intended complex oxide catalyst is for use in hydrogen treatment, any of the methods and conditions disclosed in JP-A-59-69149, Patent Registration Nos. 3599265, 1342772 and 2986838, JP-A-2007-152324, etc. may be appropriately employed.

In the process for producing the complex oxide catalyst of the present invention, the aqueous slurry obtained by mixing the complex oxide containing predetermined amounts of molybdenum and cobalt, with the acid and water is dried and is then calcined. However, preferably, the resulting catalyst is subjected to a heat treatment in the presence of a reducing substance (hereinafter optionally simply referred to as "a reduction treatment"), after the calcining. This reduction treatment is effective to improve the catalytic activity of the catalyst. This effect is remarkable particularly when the catalyst for use in production of unsaturated aldehyde and unsaturated carboxylic acid is produced.

Preferable examples of the reducing substance include hydrogen, ammonia, carbon monoxide, hydrocarbon, alcohol, aldehyde, amine and the like. In this regard, the number of carbon atoms in each of hydrocarbon, alcohol, aldehyde and amine is preferably from 1 to 6. Examples of $C_{1-6}$ hydrocarbon include saturated aliphatic hydrocarbons such as methane, ethane, propane, n-butane and isobutane; unsaturated aliphatic hydrocarbons such as ethylene, propylene, α-butylene, β-butylene and isoputylene; and benzene. Examples of $C_{1-6}$ alcohol include saturated aliphatic alcohols such as methyl alcohol, ethyl alcohol, n-propyl alcohol, isopropyl alcohol, n-butyl alcohol, isobutyl alcohol, secondary butyl alcohol and alcohol; unsaturated aliphatic alcohols such as allyl alcohol, crotyl alcohol and methallyl alcohol; and phenols. Examples of $C_{1-6}$ aldehyde include saturated aliphatic aldehydes such as formaldehyde, acetoaldehyde, propion aldehyde, n-butyl aldehyde and isobutyl aldehyde; and unsaturated aliphatic aldehydes such as acrolein, crotonaldehyde and methacrolein. Examples of $C_{1-6}$ amine include saturated aliphatic amines such as methyl amine, dimethyl amine, trimethyl amine, ethyl amine, diethyl amine and triethyl amine; unsaturated such as amine and diallyl amine; and aniline. Above all, hydrogen is preferable as the reducing substance. Each of these reducing substances may be used alone, or two or more thereof may be used in combination.

The reduction treatment is usually carried out by subjecting the catalyst to a heat treatment under an atmosphere of a gas containing the above-described reducing substance. The concentration of the reducing substance in the gas is usually from 0.1 to 50% by vol., preferably from 3 to 30% by vol. The reducing substance may be diluted with nitrogen, carbon dioxide, water, helium, argon or the like to such a concentration. In this connection, a molecular oxygen may be used, in so far as the effect of the reduction treatment is not impaired. However, no use of molecular oxygen is preferable.

The temperature for the reduction treatment (i.e., the temperature for the heat treatment in the reduction treatment) is preferably from 200 to 600° C., more preferably from 300 to 500° C. The time for the reduction treatment (i.e., the time for the heat treatment in the reduction treatment) is usually from 5 minutes to 20 hours, preferably from 30 minutes to 10 hours.

Preferably, the reduction treatment is conducted as follows: the calcined solid (or the complex oxide catalyst) obtained after the calcining is put in a tubular or box-like container, and is then reduced while a gas containing the reducing substance is allowed to flow into the container. The gas discharged from the container in this treatment may be circulated for recycling, as required. For example, the catalyst is charged in a reaction tube for use in vapor phase catalytic oxidation, and a gas containing the reducing substance is allowed to flow into the reaction tube for the reduction treatment. In this case, the catalyst may be subsequently subjected to a vapor phase catalytic oxidation.

By this reduction treatment, the mass of the calcined solid (or the complex oxide catalyst) after the calcining is usually decreased. This is considered to be attributed to a loss of the lattice oxygen from the catalyst. A rate of decrease in the mass of the catalyst due to this reduction treatment (or the heat treatment) is preferably from 0.05 to 6% by mass, more preferably from 0.1 to 5% by mass. When this rate of decrease in the mass becomes too high because of excessive reduction, the catalytic activity of the catalyst, on the contrary, sometimes tends to lower. In such a case, the catalyst is again calcined under an atmosphere of a gas containing a molecular oxygen, to thereby lower the rate of decrease in the mass. The rate of decrease in the mass of the catalyst is determined by the following equation:

Rate of decrease in mass (%)=(the mass of the catalyst found before the reduction treatment−the mass of the catalyst found after the reduction treatment)/the mass of the catalyst found before the reduction treatment×100

In this regard, the reducing substance or a decomposed product derived from the reducing substance may remain in the catalyst after the reduction treatment, depending on the kind of the reducing substance or the conditions for the heat treatment. In such a case, the mass of the residue in the catalyst is separately measured, and this measured value is subtracted from the mass of the catalyst including the residue, and the mass of the catalyst after the reduction treatment is calculated. Since the residue is typically carbon, the mass of the residue can be determined, for example, by measurement of total carbon (or TC).

After the above-described reduction treatment, if needed, the catalyst may be again calcined under an atmosphere of a molecular oxygen-containing gas (this second calcining under the atmosphere of the molecular oxygen-containing gas being optionally referred to as "re-oxidation").

The concentration of the molecular oxygen in the gas of the atmosphere for use in the re-oxidation is usually from 1 to 30% by vol., preferably from 10 to 25% by vol. As a molecular oxygen source, there is usually used an air or pure oxygen, which optionally may be diluted with nitrogen, carbon dioxide, water, helium, argon or the like for use as the molecular oxygen-containing gas. The temperature for the re-oxidation is usually from 200 to 600° C., preferably from 350 to 550° C. The time for the re-oxidation is usually from 5 minutes to 20 hours, preferably from 30 minutes to 10 hours.

In the process for producing the complex oxide catalyst of the present invention, if needed, the catalyst is molded. The molding method may be any of the conventional methods: for example, tablet molding, extrusion molding or the like is employed to shape the catalyst into rings, pellets, globular particles, granules or other desired form. The molding processing may be done in any stage, that is, before the drying, before the calcining, before the reduction treatment or after the reduction treatment. In the molding processing, inorganic fibers or the like substantially inert to an objective reaction may be added to the catalyst in order to improve the mechanical strength of the catalyst.

As described above, the complex oxide catalyst of the present invention can be obtained. The complex oxide catalyst may contain molybdenum and cobalt alone as metal elements, or may contain one or more metal elements other than molybdenum and cobalt as constitutive elements, together with molybdenum and cobalt. Examples of other metal elements constituting the complex oxide catalyst include bismuth, iron, nickel, manganese, zinc, calcium, magnesium, tin, lead, phosphorus, boron, arsenic, tellurium, tungsten, antimony, silicon, aluminum, titanium, zirconium, cerium, potassium, rubidium, cesium, thallium, vanadium, copper, silver, lanthanum, etc.

The above-described complex oxide catalyst is preferably one represented by the following formula (I):

$$Mo_aBi_bFe_cCo_dA_eB_fC_gO_x \qquad (I)$$

wherein, in the formula (I), Mo, Bi, Fe and Co represent molybdenum, bismuth, iron and cobalt, respectively; A represents an element selected from the group consisting of nickel, manganese, zinc, calcium, magnesium, tin and lead; B represents an element selected from the group consisting of phosphorus, boron, arsenic, tellurium, tungsten, antimony, silicon, aluminum, titanium, zirconium and cerium; C represents an element selected from the group consisting of potassium, rubidium, cesium and thallium; O represents oxygen; b, c, d, e, f and g are values satisfying the following equations, provided that a is 12 (a=12): $0<b\leq10$, $0<c\leq10$, $1\leq d\leq10$, $0\leq e\leq10$, $0\leq f\leq10$ and $0<g\leq2$; and x is a value determined by the oxidation states of the respective elements.

Among the complex oxides having the compositions of the formula (I), the complex oxides having the following compositions, excluding oxygen atoms, are preferable:

$$Mo_{12}Bi_{0.1-5}Fe_{0.5-5}Co_{5-10}Cs_{0.01-1}$$

$$Mo_{12}Bi_{0.1-5}Fe_{0.5-5}Co_{5-10}Sb_{0.1-5}K_{0.01-1}$$

The process for producing the complex oxide catalyst of the present invention is intended to produce at least one complex oxide catalyst selected from the group consisting of a catalyst for use in production of unsaturated aldehyde and unsaturated carboxylic acid, a catalyst for use in production of unsaturated carboxylic acid, a catalyst for use in production of unsaturated nitrile, and a catalyst for use in hydrogen treatment. Above all, the process of the present invention is suitable for production of the catalyst for use in production of unsaturated aldehyde and unsaturated carboxylic acid.

As the catalyst for use in production of unsaturated aldehyde and unsaturated carboxylic acid, there are exemplified a catalyst for use in production of acrolein and acrylic acid by vapor phase catalytic oxidation of propylene with molecular oxygen, and a catalyst for use in production of methacrolein and methacrylic acid by vapor phase catalytic oxidation of isobutylene or tertiary butyl alcohol with molecular oxygen. As the catalyst for use in production of unsaturated carboxylic acid, there are exemplified a catalyst for use in production of acrylic acid by vapor phase catalytic oxidation of propane with molecular oxygen, a catalyst for use in production of acrylic acid by vapor phase catalytic oxidation of acrolein with molecular oxygen, and a catalyst for use in production of methacrylic acid by vapor phase catalytic oxidation of methacrolein with molecular oxygen. As the catalyst for use in production of unsaturated nitrile, there are exemplified a catalyst for use in production of acrylonitrile by vapor phase catalytic ammoxidation of propylene or propane with molecular oxygen and ammonia, and a catalyst for use in production of methacrylonitrile by vapor phase catalytic ammoxidation of isobutylene or tertiary butyl alcohol with molecular oxygen and ammonia. As the catalyst for use in hydrogen treatment, there are exemplified a catalyst for use in removal or decrease in concentration of a sulfur compound and/or a nitrogen compound in a product by reacting the sulfur compound and/or the nitrogen compound in oil fraction with hydrogen, and/or a hydrocracking catalyst to lighten heavy oil.

EXAMPLES

Hereinafter, the present invention will be described in more detail by Examples, which however should not be construed as limiting the scope of the present invention in any way.

In the following Examples, the activities of the catalysts were evaluated by the following methods.

<Catalytic Activity Test>

The catalyst (1 g) was charged in a glass reaction tube with an inner diameter of 18 mm, and a gas mixture of isobutylene/oxygen/nitrogen/steam (=1/2.2/6.2/2.0 in molar ratio) was fed to this reaction tube at a flow rate of 87.5 ml/min. (based on STP) to carry out an oxidation reaction at a reaction temperature of 400° C. for 15 hours. After that, the reaction temperature was changed to 390° C. to carry out the oxidation reaction for one hour. The gas from the outlet of the reaction tube (i.e., the gas resulting from the reaction) was analyzed by gas chromatography. A conversion of isobutylene and a total selectivity and total yield of methacrolein and methacrylic acid were calculated by the following equations.

Conversion (%) of isobutylene=[(number of moles of fed isobutylene)−(number of moles of unreacted isobutylene)]÷(number of moles of fed isobutylene)×100

Total selectivity (%) of methacrolein and methacrylic acid=(number of moles of methacrolein and methacrylic acid)÷[(number of moles of fed isobutylene)−(number of moles of unreacted isobutylene)]×100

Total yield (%) of methacrolein and methacrylic acid=(number of moles of methacrolein and methacrylic acid)÷(number of moles of fed isobutylene)×100

Reference Example 1

Preparation of New Catalyst (a)

Ammonium molybdate [$(NH_4)_6Mo_7O_{24} \cdot 4H_2O$] (441.4 parts by mass) was dissolved in warm water (500 parts by mass) to prepare a solution A. On the other hand, iron (III) nitrate [$Fe(NO_3)_3 \cdot 9H_2O$] (202.0 parts by mass), cobalt nitrate [$Co(NO_3)_2 \cdot 6H_2O$] (436.6 parts by mass) and cesium nitrate [$CsNO_3$] (19.5 parts by mass) were dissolved in warm water (200 parts by mass), and then, bismuth nitrate [$Bi(NO_3)_3 \cdot 5H_2O$] (97.0 parts by mass) was dissolved in this solution to prepare a solution B.

Next, the solution A was stirred, the solution B was added to the solution A to form slurry, and this slurry was dried at 250° C. with a flash dryer to obtain a catalyst precursor. To the catalyst precursor (100 parts by mass), silica alumina fibers (18 parts by mass) ["RFC400-SL" manufactured by ITM] and antimony trioxide [$Sb_2O_3$] (2.54 parts by mass) were added, and the resulting mixture was molded to obtain a ring-like molded article with an outer diameter of 6.3 mm, an inner diameter of 2.5 mm and a length of 6 mm. This molded article was calcined at 545° C. under a stream of an air for 6 hours, to obtain a new catalyst (a).

This new catalyst (a) contained 0.96 bismuth atom, 0.48 antimony atom, 2.4 iron atoms, 7.2 cobalt atoms, 0.48 cesium atom, 4.6 silicon atoms and 5.0 aluminum atoms per 12 molybdenum atoms.

Reference Example 2

Preparation of Spent Catalyst (b)

The new catalyst (a) was used in a vapor phase catalytic oxidation reaction of isobutylene with molecular oxygen for production of methacrolein and methacrylic acid, for a predetermined time, to obtain a spent catalyst (b).

Reference Example 3

Preparation of Complex Oxide Containing Molybdenum and Cobalt

The spent catalyst (b) (100 parts by mass) was ground and was then added to and mixed into water (200 parts by mass) and a 25% by mass aqueous ammonia solution (272 parts by mass). This mixture with its liquid temperature maintained at 40° C. was stirred for one hour and was then filtered under reduced pressure to obtain a filtrate. This filtrate was subjected to a heat treatment at 420° C. in an air for 2 hours, to obtain a complex oxide (61.78 parts by mass) as a recovered product.

A part of this complex oxide was subjected to an elemental analysis with a fluorescent X-ray analyzer ("ZSX Primus II" manufactured by Rigaku Innovative Technologies, Inc.). As a result, the complex oxide was found to contain 48.00% by mass of molybdenum, 19.30% by mass of cobalt and 2.94% by mass of cesium.

Example 1

Preparation and Evaluation of Complex Oxide Catalyst (1)

The above-described complex oxide (30 parts by mass) was ground and was then added to and mixed into water (25 parts by mass) and 60% by mass nitric acid (32 parts by mass). This aqueous slurry with its liquid temperature maintained at 50° C. was stirred for one hour. After that, to this aqueous slurry still being stirred, cesium nitrate [$CsNO_3$] (0.27 part by mass), iron (III) nitrate [Fe $(NO_3)_3.9H_2O$] (16.19 parts by mass), cobalt nitrate [$Co(NO_3)_2.6H_2O$] (6.40 parts by mass) and bismuth nitrate [$Bi(NO_3)_3.5H_2O$] (7.78 parts by mass) were added, to prepare a solution C.

On the other hand, ammonium molybdate [$(NH_4)_6Mo_7O_{24}.4H_2O$] (8.88 parts by mass) was dissolved in a mixture of a 25% by mass aqueous ammonia solution (8.76 parts by mass) and water (100 parts by mass) to prepare a solution D.

Next, the solution D was stirred, and the solution C was added to the solution D to obtain aqueous slurry. Then, this aqueous slurry was transferred to a stainless steel container and was dried at 250° C. in a bin dryer, to obtain a catalyst precursor. This catalyst precursor was subjected to tablet compression under a pressure of about 40 MPa and was then ground. The resulting grains were screened with a sieve with an opening of from 2 mm to 710 μm to obtain granules with a size of from 2 mm to 710 μm. This granular catalyst precursor was calcined at 525° C. under a stream of an air for 6 hours, to obtain a complex oxide catalyst (1). This complex oxide catalyst (1) contained 0.96 bismuth atom, 2.5 iron atoms, 7.2 cobalt atoms and 0.49 cesium atom per 12 molybdenum atoms.

The catalytic activity of this complex oxide catalyst (1) was evaluated according to the above-described catalytic activity test. As a result, the conversion of isobutylene was 77.4%; the total selectivity of methacrolein and methacrylic acid was 85.5%; and the total yield of methacrolein and methacrylic acid was 66.2%.

Comparative Example 1

Preparation and Evaluation of New Catalyst (R1)

To confirm an influence of the use of the molybdenum- and cobalt-containing complex oxide on a catalytic activity, a new catalyst (R1) was prepared as follows, using new raw materials, so as to have the same catalyst composition as that of the above-described complex oxide catalyst (1). Then, the catalytic activity of the new catalyst (R1) was evaluated.

Ammonium molybdate [$(NH_4)_6Mo_7O_{24}.4H_2O$] (441.4 parts by mass) was dissolved in warm water (500 parts by mass) to prepare a solution E.

On the other hand, iron (III) nitrate [$Fe(NO_3)_3.9H_2O$] (202.0 parts by mass), cobalt nitrate [$Co(NO_3)_2.6H_2O$] (436.6 parts by mass) and cesium nitrate [$CsNO_3$] (19.5 parts by mass) were dissolved in warm water (200 parts by mass), and then, bismuth nitrate [$Bi(NO_3)_3.5H_2O$] (97.0 parts by mass) was dissolved in this solution to prepare a solution F.

Next, the solution E was stirred, and the solution F was added to the solution E to obtain aqueous slurry. Then, this aqueous slurry was transferred to a stainless steel container and was dried at 250° C. in a bin dryer, to obtain a catalyst precursor. This catalyst precursor was subjected to tablet compression under a pressure of about 40 MPa and was then ground. The resulting grains were screened with a sieve with an opening of from 2 mm to 710 μm to obtain granules with a size of from 2 mm to 710 μm. This granular catalyst precursor was calcined at 525° C. under a stream of an air for 6 hours, to obtain a new catalyst (R1). This new catalyst (R1) contained 0.96 bismuth atom, 2.4 iron atoms, 7.2 cobalt atoms and 0.48 cesium atom per 12 molybdenum atoms.

The catalytic activity of this new catalyst (R1) was evaluated according to the above-described catalytic activity test. As a result, the conversion of isobutylene was 75.6%; the total selectivity of methacrolein and methacrylic acid was 86.5%; and the total yield of methacrolein and methacrylic acid was 65.4%.

Comparative Example 2

Preparation and Evaluation of Complex Oxide Catalyst (R2)

The spent catalyst (b) prepared in Example 1 was used for the following recovery test under the same conditions as those described in Example 1 of the pamphlet of International Publication No. WO 2007/032228 A1. The recovered molybdenum was used to prepare a complex oxide catalyst. The spent catalyst (b) (600 parts by mass) was ground and was then dispersed in pure water (2,400 parts by mass), and a 45% by mass aqueous sodium hydroxide solution (800 parts by mass) was added to the resulting dispersion. The resulting mixture was stirred at 60° C. for 3 hours, and the insoluble matter was separated therefrom by filtration, to obtain a catalyst component-containing aqueous solution. To the catalyst component-containing aqueous solution, a 36% by mass hydrochloric acid was added to adjust the pH of the aqueous solution to 1.0. Then, the aqueous solution was maintained at 30° C. for 3 hours under stirring. The resulting precipitate was separated by filtration and was rinsed with a 2% by mass aqueous ammonium nitrate solution, to obtain a catalyst component-containing precipitate (425 parts by mass). This precipitate was not calcined under an air atmosphere. A part of this precipitate was subjected to an elemental analysis in the same manner as in Reference Example 3 of the present application, and was then found to contain 60.1% by mass of molybdenum, 0.7% by mass of cobalt and 6.3% by mass of cesium.

The catalyst component-containing precipitate (30.0 parts by mass) was ground and was then added to and mixed into water (25.0 parts by mass) and 60% by mass nitric acid (3.35 parts by mass), to obtain aqueous slurry. This aqueous slurry was stirred for one hour with its liquid temperature maintained at 50° C. After that, cesium nitrate [$CsNO_3$] (0.18 part by mass), iron (III) nitrate [$Fe(NO_3)_3.9H_2O$] (30.37 parts by mass) and cobalt nitrate [$Co(NO_3)_2.6H_2O$] (64.59 parts by mass) were added to and dissolved in the aqueous slurry under stirring. Then, bismuth nitrate [$Bi(NO_3)_3.5H_2O$] (14.59 parts by mass) was added to and dissolved in the solution. The resulting solution was referred to as a solution G. On the other hand, ammonium molybdate [$(NH_4)_6Mo_7O_{24}.4H_2O$] (33.18 parts by mass) was dissolved in a 25% by mass aqueous ammonia solution (10.97 parts by mass) and water (100 parts by mass) to obtain a solution H.

Next, the solution H was stirred, and the solution G was added to the solution H to form aqueous slurry. Then, this aqueous slurry was transferred to a stainless steel container and was dried at 250° C. in a bin dryer, to obtain a catalyst precursor. This catalyst precursor was subjected to tablet compression under a pressure of about 40 MPa and was then ground. The resulting grains were screened with a sieve with an opening of from 2 mm to 710 μm to obtain granules with a size of from 2 mm to 710 μm. This granular catalyst precursor was calcined at 525° C. under a stream of an air for 6 hours, to obtain a complex oxide catalyst (R2). This complex oxide catalyst (R2) was found to contain 0.96 bismuth atom, 2.5 iron atoms, 7.2 cobalt atoms and 0.49 cesium atom per 12 molybdenum atoms.

The catalytic activity of this complex oxide catalyst (R2) was evaluated according to the above-described catalytic activity test. As a result, the conversion of isobutylene was 71.8%; the total selectivity of methacrolein and methacrylic acid was 83.9%; and the total yield of methacrolein and methacrylic acid was 60.2%.

Example 2

Preparation and Evaluation of Complex Oxide Catalyst (2)

The complex oxide catalyst (1) (10.00 g) obtained in Example 1 was charged in a glass reaction tube and was then subjected to a reduction treatment at 375° C. for 8 hours, while a gas mixture of hydrogen/steam/nitrogen (=5/10/85 in molar ratio) was being fed into this glass reaction tube at a flow rate of 200 mL/min. (based on STP). A rate of decrease in the mass of the catalyst attributed to this reduction treatment was 0.8%. After that, the catalyst was re-oxidized by heating at 350° C. for one hour under a stream of an air, to obtain a complex oxide catalyst (2).

The catalytic activity of this complex oxide catalyst (2) was evaluated according to the above-described catalytic activity test. As a result, the conversion of isobutylene was 81.3%; the total selectivity of methacrolein and methacrylic acid was 85.9%; and the total yield of methacrolein and methacrylic acid was 69.8%.

What is claimed is:

1. A process for producing a complex oxide catalyst containing molybdenum and cobalt, comprising preparing an aqueous slurry by mixing a complex oxide containing molybdenum and cobalt with an acid and water; drying the aqueous slurry to obtain a dried solid; calcining the dried solid, and subjecting the calcined dried solid to a heat treatment in the presence of a reducing substance;

wherein the complex oxide is obtained by mixing a molybdenum- and cobalt-containing complex oxide catalyst which has been used in a vapor phase catalytic oxidation reaction with an aqueous extracting solution obtained by dissolving at least one of ammonia and an organic base in water, thereby extracting molybdenum and cobalt into the aqueous phase; drying the aqueous phase to obtain a dried solid, and calcining the dried solid under an atmosphere of an oxidizing gas to obtain the complex oxide.

2. The process according to claim 1, wherein a ratio of molybdenum to cobalt in said complex oxide is from 1:12 to 12:1 in molar ratio.

3. The process according to claim 1, wherein said complex oxide contains at least one element selected from the group consisting of potassium, rubidium, cesium and thallium.

4. The process according to claim 1, wherein the amount of said acid to be used is from 1 to 20 moles per one mole of cobalt in said complex oxide.

5. The process according to claim 1, wherein said acid is an inorganic acid.

6. The process according to claim 1, wherein said acid is nitric acid.

7. The process according to claim 1, wherein said complex oxide catalyst is for use in production of unsaturated aldehyde and unsaturated carboxylic acid.

8. The process according to claim 1, wherein said complex oxide catalyst is represented by the following formula (I):

$$Mo_aBi_bFe_cCo_dA_eB_fC_gO_x \qquad (I)$$

wherein, in the formula (I), Mo, Bi, Fe and Co represent molybdenum, bismuth, iron and cobalt, respectively; A represents an element selected from the group consisting of nickel, manganese, zinc, calcium, magnesium, tin and lead; B represents an element selected from the group consisting of phosphorus, boron, arsenic, tellurium, tungsten, antimony, silicon, aluminum, titanium, zirconium and cerium; C represents an element selected from the group consisting of potassium, rubidium, cesium and thallium; O represents oxygen; b, c, d, e, f and g are values satisfying the following equations, provided that a is 12 (a=12): $0<b\leqq10$, $0<c\leqq10$, $1\leqq d\leqq10$, $0\leqq e\leqq10$, $0\leqq f\leqq10$ and $0<g\leqq2$; and x is a value determined by the oxidation states of the respective elements.

9. The process according to claim 1, wherein said heat treatment is carried out at a temperature of from 200 to 600° C.

10. The process according to claim 1, wherein a rate of decrease in mass attributed to said heat treatment is from 0.05 to 6% by mass.

11. The process according to claim 1, wherein said reducing substance is hydrogen.

* * * * *